(12) United States Patent
Sela et al.

(10) Patent No.: US 10,493,122 B2
(45) Date of Patent: Dec. 3, 2019

(54) SUBLINGUAL DELIVERY OF GLATIRAMER ACETATE

(71) Applicant: MAPI PHARMA LTD., Ness Ziona (IL)

(72) Inventors: Yoram Sela, Ra'anana (IL); Ehud Marom, Tel Aviv (IL); Nadav Bleich Kimelman, Jerusalem (IL)

(73) Assignee: MAPI PHARMA LTD., Ness Ziona (IL)

( * ) Notice: Subject to any disclaimer, the term of this patent is extended or adjusted under 35 U.S.C. 154(b) by 0 days.

(21) Appl. No.: 15/126,362

(22) PCT Filed: Mar. 16, 2015

(86) PCT No.: PCT/IL2015/050275
§ 371 (c)(1),
(2) Date: Sep. 15, 2016

(87) PCT Pub. No.: WO2015/140790
PCT Pub. Date: Sep. 24, 2015

(65) Prior Publication Data
US 2017/0080044 A1    Mar. 23, 2017

Related U.S. Application Data

(60) Provisional application No. 61/953,945, filed on Mar. 17, 2014.

(51) Int. Cl.
| A61K 38/03 | (2006.01) |
| A61K 47/10 | (2017.01) |
| A61K 9/00 | (2006.01) |
| A61K 9/20 | (2006.01) |
| A61K 9/12 | (2006.01) |

(52) U.S. Cl.
CPC .............. *A61K 38/03* (2013.01); *A61K 9/006* (2013.01); *A61K 9/12* (2013.01); *A61K 9/2013* (2013.01); *A61K 9/2018* (2013.01); *A61K 9/2027* (2013.01); *A61K 9/2059* (2013.01); *A61K 47/10* (2013.01)

(58) Field of Classification Search
CPC .... A61K 9/006; A61K 9/2013; A61K 9/2018; A61K 9/2027; A61K 9/2059; A61K 38/03; A61K 47/10
See application file for complete search history.

(56) References Cited

U.S. PATENT DOCUMENTS

| 6,977,070 B2 | 12/2005 | Dugger, III |
| 7,022,663 B2 | 4/2006 | Gilbert et al. |
| 8,377,885 B2 | 2/2013 | Marom et al. |
| 2001/0055568 A1 | 12/2001 | Gilbert et al. |
| 2005/0170004 A1* | 8/2005 | Rosenberger .......... A61K 9/145 424/490 |
| 2005/0214251 A1 | 9/2005 | Pohl et al. |
| 2007/0065492 A1 | 3/2007 | Bodor |
| 2008/0090897 A1* | 4/2008 | Steiner ................. A61K 31/366 514/453 |
| 2009/0053176 A1 | 2/2009 | Ahlberg et al. |
| 2012/0263764 A1 | 10/2012 | Watson |
| 2016/0193276 A1* | 7/2016 | Geister .................. A61K 9/006 424/465 |

FOREIGN PATENT DOCUMENTS

| WO | 2006004749 A2 | 1/2006 |
| WO | 2008120207 A2 | 10/2008 |
| WO | 2010011879 A2 | 1/2010 |
| WO | 2010032140 A2 | 3/2010 |
| WO | 2011/080733 A1 | 7/2011 |
| WO | 2014/100639 A1 | 6/2014 |
| WO | 2014/100643 A1 | 6/2014 |

OTHER PUBLICATIONS

Guo et al., Evaluation of a Rat Model of Experimental Autoimmune Encephalomyelitis with Human MBP as Antigen. Cellular & Molecular Immunology, vol. 1, No. 5, Oct. 2004, pp. 387-391 (5 pages).
Moingeon et al., Immune mechanisms of allergen-specific sublingual immunotherapy. Allergy 2016, 61(2), pp. 151-165 (15 pages).
Sorensen et al., Intravenous immunoglobulin G reduces MRI activity in relapsing multiple sclerosis. Neurology 50(5), May 1998, pp. 1273-1281 (9 pages).

* cited by examiner

*Primary Examiner* — Michael B. Pallay
(74) *Attorney, Agent, or Firm* — Rothwell, Figg, Ernst & Manbeck, P.C.

(57) ABSTRACT

The present invention provides Glatiramer acetate compositions in a non-gelling matrix, formulated for sublingual delivery.

8 Claims, 2 Drawing Sheets

SUBLINGUAL DELIVERY OF GLATIRAMER ACETATE

CROSS REFERENCE TO RELATED APPLICATION

This application is a 35 U.S.C. 371 National Phase Entry Application from PCT/IL2015/050275, filed Mar. 16, 2015, which claims the benefit of U.S. Provisional Application No. 61/953,945 filed on Mar. 17, 2014, the disclosure of which are incorporated by reference in their entirety.

FIELD OF THE INVENTION

The present invention provides formulations of Glatiramer acetate (Copolymer 1, Cop-1, Copaxone) for non-invasive, sublingual delivery.

BACKGROUND OF THE INVENTION

Medicaments taken by mouth and swallowed are absorbed first into the blood perfusing the gastrointestinal (GI) tract. The venous drainage from the GI tract is first passed into the blood perfusing the liver. This means that medicaments absorbed from the lumen of the gastrointestinal tract are immediately presented to the liver, the major detoxifying organ of the body. In addition to protecting the organism from ingested toxins, the liver also metabolizes medicaments, which may be inactivated by first pass metabolism in the liver. Blood from the liver then returns to the left side of the heart via the hepatic portal vein and reaches the rest of the systemic circulation. This first pass through the liver may result in the removal of a substantial proportion of an ingested medicament.

Accordingly, other routes of drug administration have been investigated, including those involving transport across the mucous membranes. Of the various mucous membranes (e.g., oral, rectal, vaginal, ocular, nasal), drug delivery via the mucous membranes in the oral cavity seems to be the most easily tolerated by patients. In addition to avoiding the problems with traditional oral administration, drug delivery via the mucous membranes of the oral cavity has certain other advantages, due to the properties of the oral mucosa itself. For example, the mucous membranes of the oral cavity are highly vascularized and well supplied with lymphatic drainage sites.

In general, the mucous membranes of the oral cavity can be divided into five main regions: the floor of the mouth (sublingual), the cheeks (buccal), the gums (gingival), the roof of the mouth (palatal), and the lining of the lips. These regions differ from each other with respect to their anatomy, drug permeability, and physiological response to drugs. For example, in terms of relative permeability, the sublingual region is more permeable than the buccal region, which is more permeable than the palatal region. This permeability is generally related to the relative thickness and degree of keratinization of these membranes, with the sublingual mucosa being relatively thin and non-keratinized, the buccal mucosa being thicker and non-keratinized, and the palatal mucosa being intermediate in thickness, but keratinized.

Several formulations for sublingual administration are known in the art; sublingual tablets (regular or fast-disintegrating), bio-adhesive sublingual tablets, lipid matrix sublingual tablets, thin films and sublingual sprays.

As described above, sublingual administration has certain advantages over oral administration. Being more direct, it is often faster acting, and it ensures that the substance will risk degradation only by salivary enzymes before entering the bloodstream, whereas orally administered drugs must survive passage through the hostile environment of the gastrointestinal tract, which risks degrading them, either by stomach acid or bile, or by the many enzymes therein, such as various peptidases, and other proteolytic enzymes as well as other enzymes such as monoamine oxidase (MAO). Furthermore, after absorption from the gastrointestinal tract, such drugs must pass to the liver, where they may be extensively altered; this is known as the first pass effect of drug metabolism. Due to the digestive activity of the stomach and intestines and the solubility of the GI tract, the oral route is unsuitable or very inefficient for some of the very important drugs widely used by patients. In addition, due to the more effective absorption, it is in some cases possible to reduce the dosage of the drug.

There is growing evidence that the sublingual mucosa contains an abundance of immune system cells, such as Langerhans-like dendritic cells which act as antigen presenting cells (APC) to T-cells in the cervical lymph nodes. Those cells are utilized for sublingual immune therapy mainly as anti-allergy treatment. As the suspected mechanism of Glatiramer acetate is through local immune response to the injected drug which is presented to T-cells in the subcutaneous tissue by APC the same mechanism will apply in the current invention (Moingeon P, Batard T, Fadel R, Frati F, Sieber J, Van Overtvelt L 2006. "Immune mechanisms of allergen-specific sublingual immunotherapy". Allergy 61 (2): 151-65).

Glatiramer acetate is the generic name for the drug COPAXONE® or Copolymer 1, developed by Teva Pharmaceuticals. It is an immunomodulator, licensed in much of the world for reduced frequency of relapses in relapsing-remitting multiple sclerosis. Copaxone is administered by subcutaneous injection at a dose of 20 mg per day or 40 mg every other day. It is a non-interferon and non-steroidal medication.

Glatiramer acetate, the active ingredient of COPAXONE®, consists of the acetate salts of synthetic polypeptides, containing four naturally occurring amino acids: L-glutamic acid, L-alanine, L-tyrosine, and L-lysine with an average molar fraction of 0.141, 0.427, 0.095, and 0.338, respectively. The average molecular weight of Glatiramer acetate is 4,700-11,000 Daltons. Chemically, Glatiramer acetate is designated L-glutamic acid polymer with L-alanine, L-lysine and L-tyrosine, acetate (salt) (CAS 147245-92-9).

Glatiramer acetate is a random polymer (average molecular mass 6.4 kD) composed of four amino acids that are found in myelin basic protein. The mechanism of action for glatiramer is unknown, although several have been proposed. Administration of glatiramer shifts the population of T cells from pro-inflammatory Th1 cells to regulatory Th2 cells that suppress the inflammatory response. Given its resemblance to myelin basic protein, glatiramer may also act as a sort of decoy, diverting an autoimmune response against myelin. The integrity of the blood-brain barrier, however, is not appreciably affected by glatiramer, at least not in the early stages of treatment. Glatiramer acetate has been shown in clinical trials to reduce the number and severity of exacerbations.

Evidence supporting the effectiveness of Glatiramer acetate in decreasing the frequency of relapses in patients with Relapsing-Remitting Multiple Sclerosis (RR-MS) derives from two placebo-controlled trials, both of which used a Glatiramer acetate dose of 20 mg/day. A comparative trial of the approved 20 mg dose and the 40 mg dose showed no significant difference in efficacy between these doses. Various clinical trials in Glatiramer acetate are on-going. This includes studies in Clinically Isolated Syndrome patients (the PreCISe study) as well as numerous combination and induction protocols, in which Glatiramer acetate is given together with or following another active product.

PCT patent publication no. WO 2014/100639 discloses an oral tablet for transmucosal delivery, comprising Glatiramer acetate in an amount from about 10% to about 60% by weight, and one or more gel forming agents in a total amount up to about 90% by weight. Gel forming agents are defined as agents which form a matrix which allows for controlled release of an active ingredient, such as carbomers, hydroxypropylcellulose, chitosan, thiolated chitosan, thiolated carbomer, ethylcellulose, gelatine, hydroxyethylcellulose, methylcellulose, carboxymethylcellulose, gummi arabicum, xanthan gum and carrageen.

There is a long felt need in the field of multiple sclerosis (MS) therapy for novel Glatiramer acetate formulations, formulated for non-invasive administration.

SUMMARY OF THE INVENTION

The present invention provides novel sublingual dosage formulations for administration of Glatiramer salts such as Glatiramer acetate. These formulations are specifically designed to provide alternative routes to the regular subcutaneous (SC) or intramuscular (IM) depot injections. Advantageously, trans-mucosal delivery using the formulations of the present invention provides a rapid uptake and response to the administered Glatiramer acetate.

WO 2014/100639 discloses formulations for transmucosal delivery of Glatiramer acetate, which comprise a gelling matrix that provides controlled release of the active ingredient across transmucosal membranes for, e.g., via buccal delivery. Such gel-forming formulations are unsuitable for immediate release of the active ingredient sublingually. It has now been surprisingly discovered that formulations containing Glatiramer acetate in a water soluble, non-gelling matrix enable efficient delivery of the active ingredient via the sublingual route. Such formulations enable immediate release of the formulation of the invention into the sublingual cavity, for immediate therapeutic benefit.

More specifically, the present invention provides, tablets, capsules, sprays and films comprising Glatiramer and/or its salts, e.g., Glatiramer acetate for administration via the oral mucosa, e.g., sublingual application.

These formulations are useful for treatment when regular, invasive alternatives are either not possible or not desirable, via a novel convenient route of delivery. According to some embodiments, the sublingual/transmucosal route of delivery may facilitate activation of the immune system as part of the Glatiramer proposed mechanism of action.

Thus, the present invention provides, in one aspect, a composition comprising a therapeutically effective amount of Glatiramer acetate in a non-gelling matrix, wherein the composition is formulated for sublingual administration.

In one embodiment, the sublingual composition comprises from about 0.5 to about 500 mg Glatiramer acetate.

In some embodiments, the sublingual composition is formulated as a sublingual tablet, sublingual capsule, sublingual film, sublingual aerosol or sublingual solution. Each possibility represents a separate embodiment of the present invention. In one currently preferred embodiment, the composition is in the form of a sublingual tablet.

In some embodiments, the non-gelling matrix comprises at least one pharmaceutically acceptable excipient selected from the group consisting of a filler, a binder, a disintegrant, a glidant, a penetration enhancer, a surfactant, a plasticizer, a buffering agent, and a lubricant. Each possibility represents a separate embodiment of the present invention.

In some embodiments, the filler is selected from the group consisting of a cellulose derivative, a sugar, a sugar alcohol and combinations thereof. In some currently preferred embodiments, the filler is mannitol, lactose or a combination thereof. Each possibility represents a separate embodiment of the present invention.

In some embodiments, the disintegrant is selected from the group consisting of starch, pregelatinized starch, crospovidone, crosslinked sodium carboxymethyl cellulose and combinations thereof. In some currently preferred embodiments, the disintegrant is starch, pregelatinized starch or a combination thereof. Each possibility represents a separate embodiment of the present invention.

In some embodiments, the binder is selected from the group consisting of polyvinylpyrrolidone (PVP), copovidone, sodium starch glycolate, and combinations thereof. In a currently preferred embodiment, the binder is polyvinylpyrrolidone (PVP). Each possibility represents a separate embodiment of the present invention.

In some embodiments, the lubricant is selected from the group consisting of magnesium stearate, calcium stearate, zinc stearate, glyceryl behenate, mineral oil, polyethylene glycol, sodium stearyl fumarate, stearic acid, talc, and combinations thereof. In a currently preferred embodiment, the lubricant is magnesium stearate. Each possibility represents a separate embodiment of the present invention.

In some embodiments, the buffering agent is selected from the group consisting of a metal oxide, a citrate salt, a phosphate salt, a borate salt, an ascorbate salt, an acetate salt, an alkaline starch, and combinations thereof. In some currently preferred embodiments, the buffering agent is citric acid, sodium citrate or a combination thereof. Each possibility represents a separate embodiment of the present invention.

In one currently preferred embodiment, the sublingual composition of the present invention is in the form of a sublingual tablet comprising Glatiramer acetate, lactose, mannitol, citric acid, sodium citrate, polyvinylpyrrolidone and pregelatinized starch.

In one embodiment, the non-gelling matrix is water soluble. In another embodiment, the composition provides an immediate release of the Glatiramer acetate active ingredient in the sublingual cavity.

In certain embodiments the sublingual composition further comprises a penetration enhancer that improves the sublingual/transmucosal penetration of the glatiramer acetate. In certain embodiments the sublingual composition further comprises a complexation agent that increases solubility and/or enhances stability.

In certain embodiments, the sublingual composition further comprises a cyclodextrin. In certain embodiments, the sublingual composition comprises a cyclodextrin selected from the group consisting of hydroxypropyl, hydroxyethyl, glucosyl, maltosyl, β-cyclodextrin maltotriosyl derivatives, γ-cyclodextrin maltotriosyl derivatives and any combination thereof. Each possibility represents a separate embodiment of the present invention.

In certain embodiments, the composition is formulated as a sublingual aerosol spray, further comprising a propellant. In certain embodiments, the sublingual composition comprises a propellant selected from the group consisting of C3, C4, C5, C6, C7 and C8 hydrocarbons of linear or branched configuration, and any combination thereof. In more specific embodiments, said propellant is selected from the group consisting of propane, n-butane, iso-butane, n-pentane, iso-pentane, neo-pentane and any combination thereof. Each possibility represents a separate embodiment of the present invention.

In certain embodiments, the sublingual composition further comprises a flavoring agent.

In other aspects, the present invention further provides a Glatiramer acetate sublingual composition as described above is for use in treating an autoimmune disease or disorder.

The present invention further provides a method of treatment of an autoimmune disease or disorder in a subject in need thereof, by administering to said subject the Glatiramer acetate sublingual composition described above.

The present invention further relates to the use of a Glatiramer acetate sublingual composition as described above, for the preparation of a medicament for treating an autoimmune disease or disorder.

In some embodiments, the autoimmune disease or disorder is multiple sclerosis (MS).

In other embodiments, the composition reduces the frequency of relapses in patients with relapsing-remitting multiple sclerosis (RR-MS).

In some embodiments, the composition can be used in combination with at least one active agent.

In a further aspect, the present invention further provides a method of preparing a solid sublingual composition comprising Glatiramer acetate as an active ingredient, comprising the following steps: (i) granulating Glatiramer acetate with at least one filler in a solvent; (ii) adding to the granulate obtained in step (i) at least one pharmaceutically acceptable excipient selected from the group consisting of a binder, a glidant, a surfactant, a plasticizer, a buffering agent, and a lubricant; (iii) drying the granulate obtained in step (ii); (iv) adding a disintegrant to the dry granulate obtained in step (iii); and (v) compressing into a solid dosage form. In a currently preferred embodiment, the solid dosage form is a tablet.

In one particular aspect, the method comprises the following steps: (i) granulating Glatiramer acetate with mannitol and lactose in a solvent; (ii) adding to the granulate obtained in step (i) citric acid, sodium citrate and polyvinylpyrrolidone; (iii) drying the granulate obtained in step (ii); (iv) adding pregelatinized starch to the dry granulate obtained in step (iii); and (v) compressing into a solid dosage form. In a currently preferred embodiment, the solid dosage form is a tablet.

In one embodiment, the solvent in step (i) is ethanol.

In another embodiment, the method further comprises the step of milling the dry granulate obtained in step (iii) prior to performing step (iv).

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
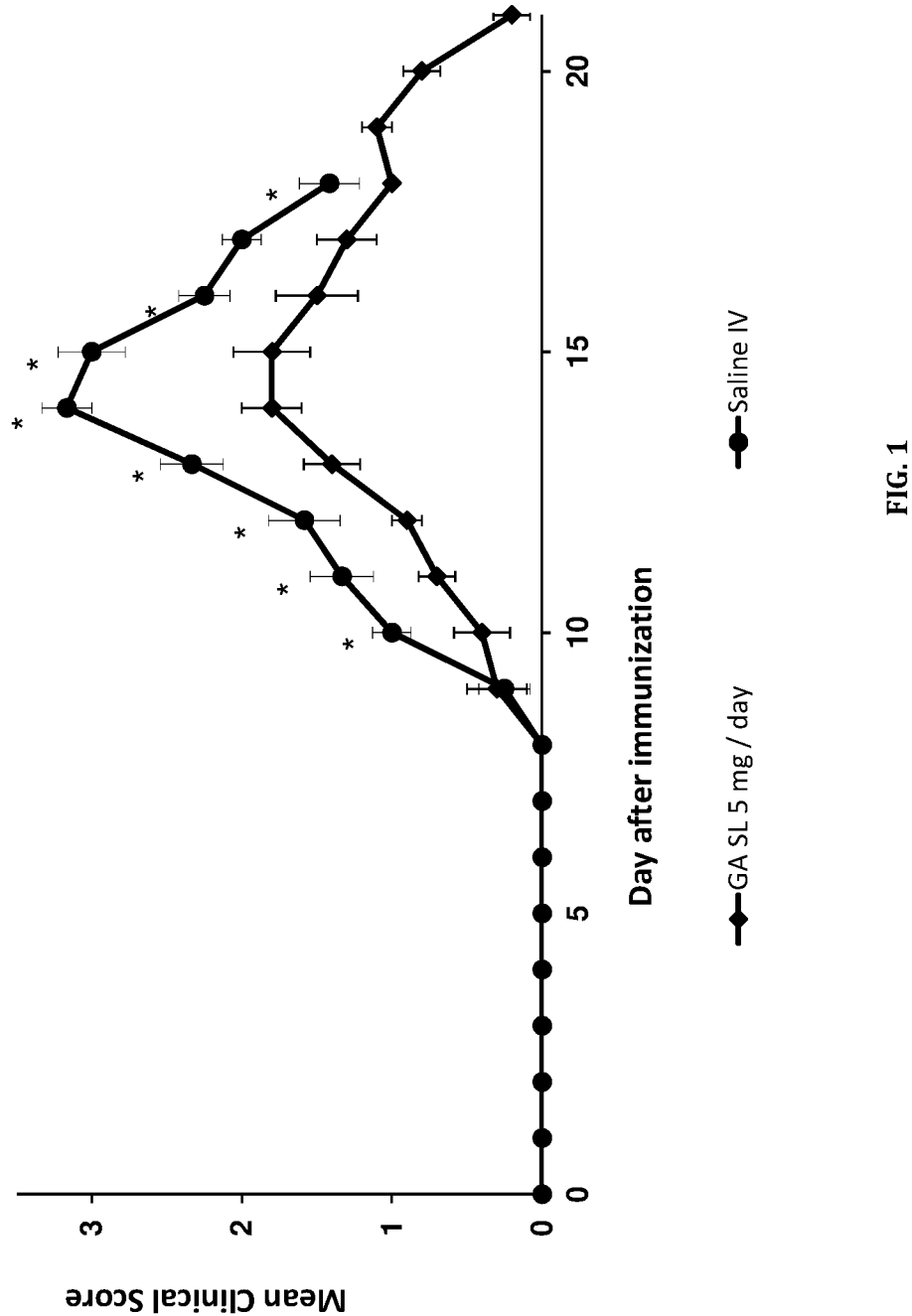
FIG. 1. Effect of Glatiramer acetate (GA) sublingual mini tablets on the clinical score in an autoimmune encephalomyelitis (EAE) guinea pig model. *$P<0.05$ Two-tailed two-sample T test assuming unequal variances, n=5 (GA SL) or 6 (Saline IV), data presented as mean±standard error.

The present invention provides, for the first time, an alternative to repeated, subcutaneous injections of Glatiramer acetate. The invention of sublingual formulations of Glatiramer acetate increases Glatiramer acetate bioavailability, as well as increasing patients' quality of life and disease management.

Sublingual Composition

The present invention provides compositions comprising a therapeutically effective amount of Glatiramer or a pharmaceutically acceptable salt thereof, in particular Glatiramer acetate, or analogs/derivatives thereof, embedded in a non-gelling matrix and formulated for sublingual administration.

The sublingual composition of the invention may be prepared in any form or shape that is suitable for sublingual administration. In some embodiments, the sublingual composition is formulated as a sublingual tablet, sublingual capsule, sublingual film, sublingual aerosol or sublingual solution. Each possibility represents a separate embodiment of the present invention. In one currently preferred embodiment, the composition is in the form of a sublingual tablet or mini tablet. The term "mini tablet" as used herein denotes a small tablet having a diameter of less than about 15 mm, e.g., a tablet that is 3-11 mm in diameter.

In accordance with the principles of the present invention, the Glatiramer or salt thereof, e.g., Glatiramer acetate, is mixed with or embedded in a soluble, non-gelling matrix and formulated in one of the dosage forms described above for sublingual administration. As used herein, the term "non-gelling matrix" means a soluble matrix that does not form a gel upon contact with the sublingual cavity. As such, the formulations of the invention differ from the formulations of WO 2014/100639 which require the presence of a gel forming agent for controlled release of the active ingredient across transmucosal membranes for, e.g., via buccal delivery. The formulations of the present invention do not contain such gel forming agent and therefore are suitable for providing immediate release of the active ingredient across the sublingual cavity, thereby enabling rapid therapeutic benefit via safe and easy administration.

As used herein, the term "immediate release" refers to formulations which release of at least 60%, more preferably 80%, more preferably at least 90% of the active ingredient in less than about one hour after administration, preferably in less than about 30 minutes after administration.

In some embodiments, the sublingual composition is formulated as a solid dosage form, e.g., sublingual tablet, sublingual capsule, sublingual film, and the like. According to the principles of the present invention, solid dosage forms generally comprise a non-gelling matrix comprising at least one pharmaceutically acceptable excipient selected from the group consisting of a filler, a binder, a disintegrant, a glidant, a penetration enhancer, a surfactant, a plasticizer, a buffering agent, and a lubricant. Each possibility represents a separate embodiment of the present invention.

Any known filler or diluent can be used in the composition of the present invention. In some non-limiting embodiments, the filler is selected from the group consisting of a cellulose derivative, a sugar, a sugar alcohol and combinations thereof. In some currently preferred embodiments, the filler is mannitol, lactose or a combination thereof. Each possibility represents a separate embodiment of the present invention.

Any known disintegrant can be used in the composition of the present invention. In some non-limiting embodiments, the disintegrant is selected from the group consisting of starch, pregelatinized starch, crospovidone, crosslinked sodium carboxymethyl cellulose and combinations thereof. In some currently preferred embodiments, the disintegrant is starch, pregelatinized starch or a combination thereof. Each possibility represents a separate embodiment of the present invention.

Any known binder can be used in the composition of the present invention. In some non-limiting embodiments, the binder is selected from the group consisting of polyvinylpyrrolidone (PVP), copovidone, sodium starch glycolate, and combinations thereof. In a currently preferred embodiment, the binder is polyvinylpyrrolidone (PVP). Each possibility represents a separate embodiment of the present invention.

Any known lubricant can be used in the composition of the present invention. In some non-limiting embodiments, the lubricant is selected from the group consisting of magnesium stearate, calcium stearate, zinc stearate, glyceryl behenate, mineral oil, polyethylene glycol, sodium stearyl fumarate, stearic acid, talc, and combinations thereof. In a currently preferred embodiment, the lubricant is magnesium stearate. Each possibility represents a separate embodiment of the present invention.

Any known buffering agent can be used in the composition of the present invention. In some non-limiting embodiments, the buffering agent is selected from the group consisting of a metal oxide, a citrate salt, a phosphate salt, a borate salt, an ascorbate salt, an acetate salt, an alkaline starch, and combinations thereof. In some currently preferred embodiments, the buffering agent is citric acid, sodium citrate or a combination thereof. Each possibility represents a separate embodiment of the present invention.

In some embodiments, the sublingual compositions of the present invention may comprise a flavoring, sweetening or taste-masking agent. Generally, any natural or synthetic flavoring agent or sweetening agent known in the art may be used in the orally dissolving formulations of the present invention. For example, suitable flavoring agents include, but are not limited to, essential oils, water soluble extracts, acesulfame potassium, talin, glycyrrhizin, sucralose, aspartame, saccharin, sodium saccharin, sodium cyclamate, aldehyde flavorings and combinations thereof. Exemplary flavorings that may be used include, but are not limited to apple, cherry, almond, cinnamon, lemon, lime, orange, mandarin, vanilla, and the like.

In addition to the aforementioned excipients, the compositions of the present invention may further comprise one or more pharmaceutically acceptable excipient(s) selected from, but not limited to, wetting agents, surfactants, emulsifying and suspending agents; preserving agents such as methyl- and propylhydroxybenzoates; colorants, moistening agents, antioxidants (e.g., ascorbic acid or sodium bisulfite), chelating agents (e.g., ethylenediaminetetraacetic acid), agents for the adjustment of tonicity such as sodium chloride, and the like. Each possibility represents a separate embodiment of the present invention.

In certain embodiments, the sublingual composition further comprises a penetration enhancer that improves the sublingual/transmucosal penetration of the Glatiramer salt. Such penetrants, for example DMSO or polyethylene glycol are generally known in the art.

In certain embodiments the sublingual composition further comprises a complexation agent that increases solubility and/or enhances stability.

In certain embodiments, the sublingual composition further comprises a cyclodextrin. In certain embodiments, the sublingual composition comprises a cyclodextrin selected from the group consisting of hydroxypropyl, hydroxyethyl, glucosyl, maltosyl, β-cyclodextrin maltotriosyl derivatives, γ-cyclodextrin maltotriosyl derivatives and any combination thereof. Each possibility represents a separate embodiment of the present invention.

In certain embodiments, the composition is formulated as a sublingual aerosol spray. In accordance with this embodiment, the formulation further comprises a propellant. Non-limiting examples of propellants include C3, C4, C5, C6, C7 and C8 hydrocarbons of linear or branched configuration, and any combination thereof. In more specific embodiments, said propellant is selected from the group consisting of propane, n-butane, iso-butane, n-pentane, iso-pentane, neo-pentane and any combination thereof. Each possibility represents a separate embodiment of the present invention.

In other embodiments, the composition is formulated as a sublingual solution. Sublingual solutions according to the present invention include aqueous solutions, alcoholic solutions, suitably flavored syrups, aqueous or oil suspensions, and flavored emulsions with edible oils such as cottonseed oil, sesame oil, coconut oil, or peanut oil, as well as elixirs, and similar pharmaceutical vehicles are included.

It is understood that any of the excipients mentioned above in the context of solid dosage forms may, as appropriate, also be used in sublingual solutions or sprays according to the principles of the present invention.

In one currently preferred embodiment, the sublingual composition of the present invention is in the form of a sublingual tablet or mini tablet comprising Glatiramer acetate, lactose, mannitol, citric acid, sodium citrate, polyvinylpyrrolidone and pregelatinized starch.

In some embodiments, the sublingual compositions of the present invention may comprise any other pharmaceutically acceptable salt of glatiramer including, but not limited to, sulfate, pyrosulfate, bisulfate, sulfite, bisulfite, phosphate, monohydrogenphosphate, dihydrogenphosphate, metaphosphate, pyrophosphate, hydrochloride, hydrobromide, hydroiodide, nitrate, propionate, decanoate, caprylate, acrylate, formate, isobutyrate, caprate, heptanoate, propiolate, oxalate, malonate, succinate, tocopheryl succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, β-hydroxybutyrate, glycolate, tartrate, methanesulfonate, propanesulfonate, naphthalene-2-sulfonate, p-toluenesulfonate, mandelate and the like salts. Each possibility represents a separate embodiment of the invention.

The term "therapeutically effective amount" as used herein is intended to qualify the amount of Glatiramer or salt thereof, e.g., Glatiramer acetate, that will achieve the goal of alleviation of the symptoms of an autoimmune disease, for example multiple sclerosis. Suitable doses include, but are not limited to, from about 0.5 to about 500 mg Glatiramer or salt thereof for each dosage form. It is understood that the amount of the Glatiramer salt administered will be determined by a physician, according to various parameters including the chosen route of administration, the age, weight, and the severity of the patient's symptoms. According to various embodiments of the present invention, the therapeutically effective amount of Glatiramer acetate ranges from about 1 mg to about 500 mg/day. Alternatively, such therapeutically effective amounts of Glatiramer acetate are from about 20 mg to about 100 mg/day.

The compositions of the present invention can be prepared by any manner known in the art. Solid dosage forms (e.g., sublingual tablets or capsules) can be prepared by wet granulation, dry granulation, direct compression, and the like. In one example involving a wet granulation process and Glatiramer acetate as an active ingredient, the compositions of the invention are prepared by a method comprising the steps of: (i) granulating Glatiramer acetate with at least one filler in a solvent; (ii) adding to the granulate obtained in step (i) at least one pharmaceutically acceptable excipient selected from the group consisting of a binder, a glidant, a surfactant, a plasticizer, a buffering agent, and a lubricant; (iii) drying the granulate obtained in step (ii); (iv) adding a disintegrant to the dry granulate obtained in step (iii); and (v) compressing into a solid dosage form. In a currently preferred embodiment, the solid dosage form is a tablet.

In one particular aspect, the method comprises the following steps: (i) granulating Glatiramer acetate with mannitol and lactose in a solvent; (ii) adding to the granulate obtained in step (i) citric acid, sodium citrate and polyvinylpyrrolidone; (iii) drying the granulate obtained in step (ii); (iv) adding pregelatinized starch to the dry granulate obtained in step (iii); and (v) compressing into a solid dosage form. In a currently preferred embodiment, the solid dosage form is a tablet.

In one embodiment, the solvent in step (i) is ethanol.

In another embodiment, the method further comprises the step of milling the dry granulate obtained in step (iii) prior to performing step (iv).

Therapeutic Use

The sublingual compositions of the present invention as well as the pharmaceutical compositions comprising same are useful for the treatment of autoimmune diseases. Autoimmune diseases within the scope of the present invention include, but are not limited to, multiple sclerosis, autoimmune hemolytic anemia, autoimmune oophoritis, autoimmune thyroiditis, autoimmune uveoretinitis, Crohn's disease, chronic immune thrombocytopenic purpura, colitis, contact sensitivity disease, diabetes mellitus, Graves disease, Guillain-Barre's syndrome, Hashimoto's disease, idiopathic myxedema, myasthenia gravis, psoriasis, pemphigus vulgaris, rheumatoid arthritis, and systemic lupus erythematosus. Each possibility represents a separate embodiment of the present invention.

Currently preferred is the treatment of multiple sclerosis (MS), including Relapsing-Remitting multiple sclerosis (RRMS). The term "multiple sclerosis" as used herein refers to an autoimmune disease of the central nervous system which is accompanied by one or more of the following symptoms: reduced or loss of vision, stumbling and uneven gait, slurred speech, as well as urinary frequency and incontinence. Additional symptoms include mood changes and depression, muscle spasms and severe paralysis. The term "treating" as used herein refers to suppression or alleviation of any of the described symptoms.

In some embodiments, the sublingual compositions of the present invention are used to reduce the frequency of relapses in patients with Relapsing-Remitting Multiple Sclerosis.

Encompassed by the present invention is a combination therapy of the sublingual compositions disclosed herein with at least one other active agent. Active agents within the scope of the present invention include, but are not limited to interferons, e.g. pegylated or non-pegylated α-interferons, or β-interferons, e.g. interferon β-1a or interferon β-1b, or τ-interferons; immunosuppressants optionally with antiproliferative/antineoplastic activity, e.g. mitoxantrone, methotrexate, azathioprine, cyclophosphamide, or steroids, e.g. methylprednisolone, prednisone or dexamethasone, or steroid-secreting agents, e.g. ACTH; adenosine deaminase inhibitors, e.g. cladribine; IV immunoglobulin G (e.g. as disclosed in *Neurology*, 1998, May 50(5):1273-81) monoclonal antibodies to various T-cell surface markers, e.g. natalizumab (ANTEGREN®) or alemtuzumab; TH2 promoting cytokines, e.g. IL-4, IL-10, or compounds which inhibit expression of TH1 promoting cytokines, e.g. phosphodiesterase inhibitors, e.g. pentoxifylline; antispasticity agents including baclofen, diazepam, piracetam, dantrolene, lamotrigine, rifluzole, tizanidine, clonidine, beta blockers, cyproheptadine, orphenadrine or cannabinoids; AMPA glutamate receptor antagonists, e.g. 2,3-dihydroxy-6-nitro-7-sulfamoylbenzo(f)quinoxaline, 1,2,3,4-tetrahydro-7-morpholinyl-2,3-dioxo-6-(trifluoromethyl)quinoxalin-1-yl] methylphosphonate, 1-(4-aminophenyl)-4-methyl-7,8-methylene-dioxy-5H-2,3-benzodiazepine, or (−)1-(4-aminophenyl)-4-methyl-7,8-methylene-dioxy-4,5-dihydro-3-methylcarbamoyl-2,3-benzodiazepine; inhibitors of VCAM-1 expression or antagonists of its ligand, e.g. antagonists of the α4β1 integrin VLA-4 and/or α-4-β-7 integrins; anti-macrophage migration inhibitory factor (Anti-MIF); xii) Cathepsin S inhibitors; xiii) mTor inhibitors. Each possibility represents a separate embodiment of the invention. Currently preferred one other active agent is FTY720 (2-amino-2-[2-(4-octylphenyl)ethyl] propane-1,3-diol; fingolimod) or its pharmaceutically acceptable salts belonging to the class of immunosuppressants. Each possibility represents a separate embodiment of the present invention.

The following examples are presented in order to more fully illustrate some embodiments of the invention. They should, in no way be construed, however, as limiting the broad scope of the invention.

EXAMPLES

Example 1. Preparation of Sublingual Tablets Containing Glatiramer Acetate

Glatiramer acetate is dissolved in double distilled water, and used in a wet granulation process together with mannitol/lactose 1:1 mixture and then dried for 1 hour in a Glatt fluid bed dryer inlet at a temperature of 30° C.

The dry mannitol/lactose/Glatiramer mixture is further mixed with additional amount of mannitol, sodium citrate and citric acid, lemon flavor, corn starch and magnesium stearate.

Sublingual Glatiramer acetate containing tablets are then prepared, containing between 5 to 20 mg Glatiramer acetate per tablet.

Example 2. Preparation of Sublingual Tablets Containing Glatiramer Acetate

Glatiramer acetate is dry-mixed with mannitol and/or lactose. The mixture is further mixed with additional amount of mannitol, sodium citrate, citric acid, lemon flavor, corn starch and magnesium stearate.

Sublingual Glatiramer acetate containing tablets are then prepared, containing between 5 to 20 mg Glatiramer acetate per tablet.

Example 3. Preparation of Sublingual Spray Containing Glatiramer Acetate

Glatiramer acetate is reconstituted and dissolved in aqueous media composed of water/alcohol and propylene glycol in a weight ratio of 60/30/10% w/w. Then, the mixture is packed into plastic meter dosed bottles providing 5 mg of Glatiramer in each administration.

Example 4. Preparation of Sublingual Mini-Tablets Containing Glatiramer Acetate Mini tablets (30 mg/tablet) containing GA (5 mg/tablet) were prepared as described in Table 1.

TABLE 1

| Component | Weight (%) | Function |
|---|---|---|
| Glatiramer Acetate | 16.7 | Active |
| Mannitol | 52 | Filler |
| Lactose | 26 | Filler |
| Citric acid | 1 | Mild acidic buffer |
| Sodium citrate | 0.8 | Mild acidic buffer |
| PVP K25 | 1.5 | Binder |
| Pregelatinized starch | 2 | Disintegrant |

The tablets were prepared by wet granulation of mannitol, lactose and Glatiramer acetate. The resulted composition was further mixed with Citric acid, Sodium citrate, and PVP K25 in Ethanol 95%, followed by 30 min drying in a vacuum oven at room temperature, and milling through 1.2 mm screen. The dry granulate was mixed with pregelatinized starch prior to tablet compression.

Example 5. Effect of Glatiramer Acetate Mini Tables in Experimental Autoimmune Encephalomyelitis (EAE) Model Guinea Pig myelin basic protein (MBP) induced Experimental Autoimmune Encephalomyelitis (EAE) model, as formerly described in L. Guo, et. al. "Evaluation of a Rat Model of Experimental Autoimmune Encephalomyelitis with Human MBP as Antigen", *Cellular & Molecular Immunology*, 2004, 1 (5), 387-391, was used to evaluate the glatiramer acetate sublingual tablets according to the present invention. EAE is a CD4+ T cell-mediated autoimmune disease characterized by peri-vascular CD4+ T cell and mononuclear cell inflammation and subsequent primary demyelination of axonal tracks in the central nervous system (CNS), leading to progressive hind-limb paralysis. EAE provides a powerful model for the study of the pathogenesis and immune regulation of CD4+ TH1/TH17-mediated tissue damage and is generally considered to be a relevant model for the human immune-mediated demyelinating disease multiple sclerosis. EAE is the most commonly used experimental model for the human inflammatory demyelinating disease, multiple sclerosis (MS). MBP is one of the major antigens used for inducing EAE in animal models and has a central role in EAE as well as in multiple sclerosis.

Two groups of wistar rats, 6-8 weeks old with similar mean weight were included in the study: (1) a control group receiving IV saline and (2) treatment group receiving the GA SL formulation of Example 4. Animals were given food and water ad libitum throughout the experiment.

Induction of EAE: In order to induce EAE, an emulsion of Guinea Pig MBP in modified Complete Freund's Adjuvant (CFA) (Sigma-Aldrich, St. Louis, Mo., USA) was prepared. Animals were injected at both hind foot pads with 0.05 ml of emulsion containing 25 mcg guinea pig BP and 200 mcg MT (*M. tuberculosis* strain H37RA, Sigma) emulsified in equal volumes of incomplete Freund's adjuvant and PBS. Body weight was measured at days 0, 11, 13, 15, 17 and 20. EAE was assessed by clinical scoring of the rats once daily from Day 0 to Day 21 post-immunization, as detailed in Table 2.

TABLE 2

| EAE Clinical Score | |
|---|---|
| Score | Clinical Signs |
| 0 | Normal mouse; no overt signs of disease |
| 1 | Limp tail |
| 2 | Hind limb paralysis |
| 3 | Hind and front limb paralysis |
| 4 | Complete paralysis: sacrifice for humane reasons |
| 5 | Moribund state; Death by EAE |

The following calculations were derived from clinical score raw data: mean maximum score is the mean of the highest scores noted for each mouse in a specific group up to indicated day of analysis; mean disease duration and mean day of onset were calculated as follows:

$$\text{Mean Disease Duration}$$

$$\frac{\text{Sum of (day of analysis} - \text{day of disease onset for each mouse)}}{\text{(number of mice per group)}}$$

$$\text{Mean Day of Onset}$$

$$\frac{\text{(sum of day of disease onset of each mouse)}}{\text{(number of mice per group)}}$$

Area under the curve (AUC) of clinical score was calculated using Microsoft Excel and represents disease burden. The experimental design is specified in Table 3:

TABLE 3

| Experimental Design | | | | |
|---|---|---|---|---|
| Group | Test Article | Route | Dose | Days of Administration |
| 1 | GA Sublingual mini-tablets (GA SL) | SL | 5 mg | 0-17 |
| 2 | Saline | IV | N/A | 0-17 |

Data was analyzed using Microsoft Excel. Each data set was analyzed using two-tailed two-sample T test assuming unequal variances, n=5/group, +/−standard error.

Results:

As shown in FIG. 1, animals treated with GA SL mini-tablets displayed less EAE symptoms than animals treated with saline IV. At days 11-16 and 18 clinical score for the GA SL group was lower than that measured for the Saline IV group in a statistically significant manner [(P<0.05 Two-tailed two-sample T test assuming unequal variances, n=5 (GA SL) or 6 (Saline IV)].

Figure 2:
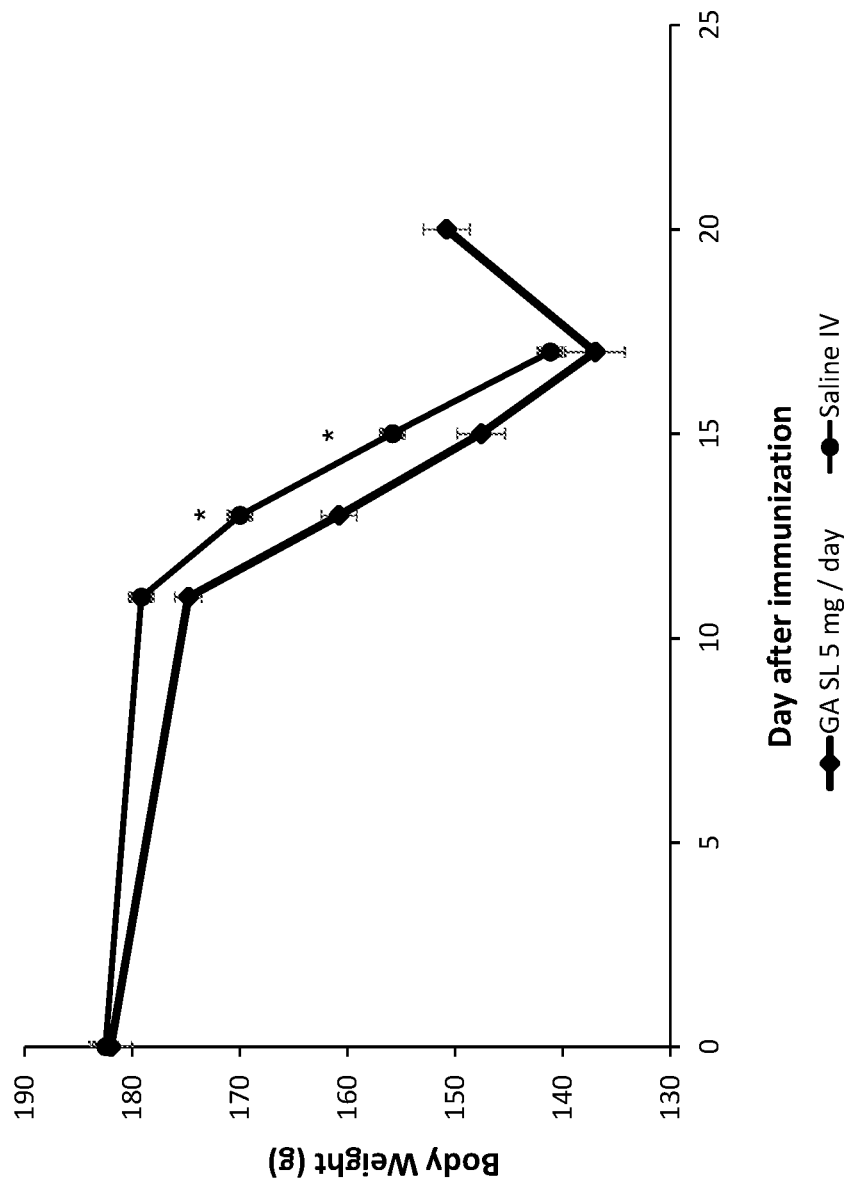
FIG. 2. Effect of Glatiramer acetate (GA) sublingual mini tablets on the body weight in an autoimmune encephalomyelitis (EAE) guinea pig model. *$P<0.05$ Two-tailed two-sample T test assuming unequal variances, n=5 (GA SL) or 6 (Saline IV), data presented as mean±standard error.

Overall body weight remained similar in both groups. At days 13 and 15, body weight in the GA SL group was statistically significant lower than that measured for the Saline IV group. However, this change is minor and is not clinically relevant [(P<0.05 Two-tailed two-sample T test assuming unequal variances, n=5 (GA SL) or 6 (Saline IV)], FIG. 2.

Both AUC of clinical score (calculated for data up to day 18) and maximum mean disease score calculated for the GA SL group were significantly lower than values calculated for the Saline IV group, as noted in Table 4.

TABLE 4

| | Calculated Values | | | |
|---|---|---|---|---|
| Groups | Maximum Mean Disease Score | Mean Disease Duration | Mean Day of Onset | AUC Clinical Score (day 18) |
| GA SL 5 mg/day | 1.90 ± 0.24* | 9.00 ± 0.44 | 10.00 ± 0.44 | 10.60 ± 1.21* |
| Saline IV | 2.71 ± 0.56 | 8.07 ± 1.50 | 8.36 ± 1.55 | 15.10 ± 2.99 |

*P < 0.05 Two-tailed two-sample T test assuming unequal variances, n = 5 (GA SL) or 6 (Saline IV), data presented +/− standard error.

The data suggests that GA SL has effect on MBP-induced EAE in rats, as clearly shown by the effect of the treatment on the clinical score, AUC of clinical score and mean disease duration. No clinically relevant effect on body weight was observed.

All references cited herein are hereby expressly incorporated by reference in their entirety. While certain embodiments of the invention have been illustrated and described, it is to be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. A method of treating an autoimmune disease or disorder in a subject in need thereof, comprising the step of administering to said subject a sublingual tablet comprising about 16.7 weight percent (wt %) Glatiramer acetate and a water-soluble non-gelling matrix comprising about 52 wt % mannitol, about 26 wt % lactose, about 2 wt % pregelatinized starch, about 1 wt % citric acid, about 0.8 wt % sodium citrate and about 1.5 wt % polyvinylpyrrolidone (PVP), wherein the sublingual tablet has a total weight of about 30 mg, wherein the non-gelling matrix does not form a gel upon contact with a sublingual cavity and provides an immediate release of the Glatiramer acetate in the sublingual cavity, and wherein the sublingual tablet is prepared by a process comprising the steps of:
   (i) wet granulating Glatiramer acetate with mannitol and lactose;
   (ii) mixing the granulate obtained in step (i) with citric acid, sodium citrate and polyvinylpyrrolidone (PVP) in ethanol;
   (iii) drying the granulate obtained in step (ii);
   (iv) milling the dry granulate obtained in step (iii);
   (v) mixing the dry granulate obtained in step (iv) with pregelatinized starch; and
   (vi) compressing the mixture of step (v) into a tablet to form the sublingual tablet.

2. The method of claim 1, wherein the sublingual tablet further comprises a flavoring agent.

3. The method of claim 1, wherein the autoimmune disease or disorder is multiple sclerosis (MS).

4. The method of claim 3, wherein the sublingual tablet reduces the frequency of relapses in patients with relapsing-remitting multiple sclerosis (RR-MS).

5. The method of claim 1, wherein the sublingual tablet provides an immediate release of at least 60% of the Glatiramer acetate in the sublingual cavity in less than one hour after administration.

6. The method of claim 5, wherein the sublingual tablet provides an immediate release of at least 80% of the Glatiramer acetate in the sublingual cavity in less than one hour after administration.

7. The method of claim 5, wherein the sublingual tablet provides an immediate release of at least 90% of the Glatiramer acetate in the sublingual cavity in less than one hour after administration.

8. The method of claim 5, wherein the sublingual tablet provides an immediate release of at least 60% of the Glatiramer acetate in the sublingual cavity in less than 30 minutes after administration.

* * * * *